April. 1, 1969 F. W. ANDERSON Plant Pat. 2,877
APRICOT TREE
Filed Sept. 14, 1967
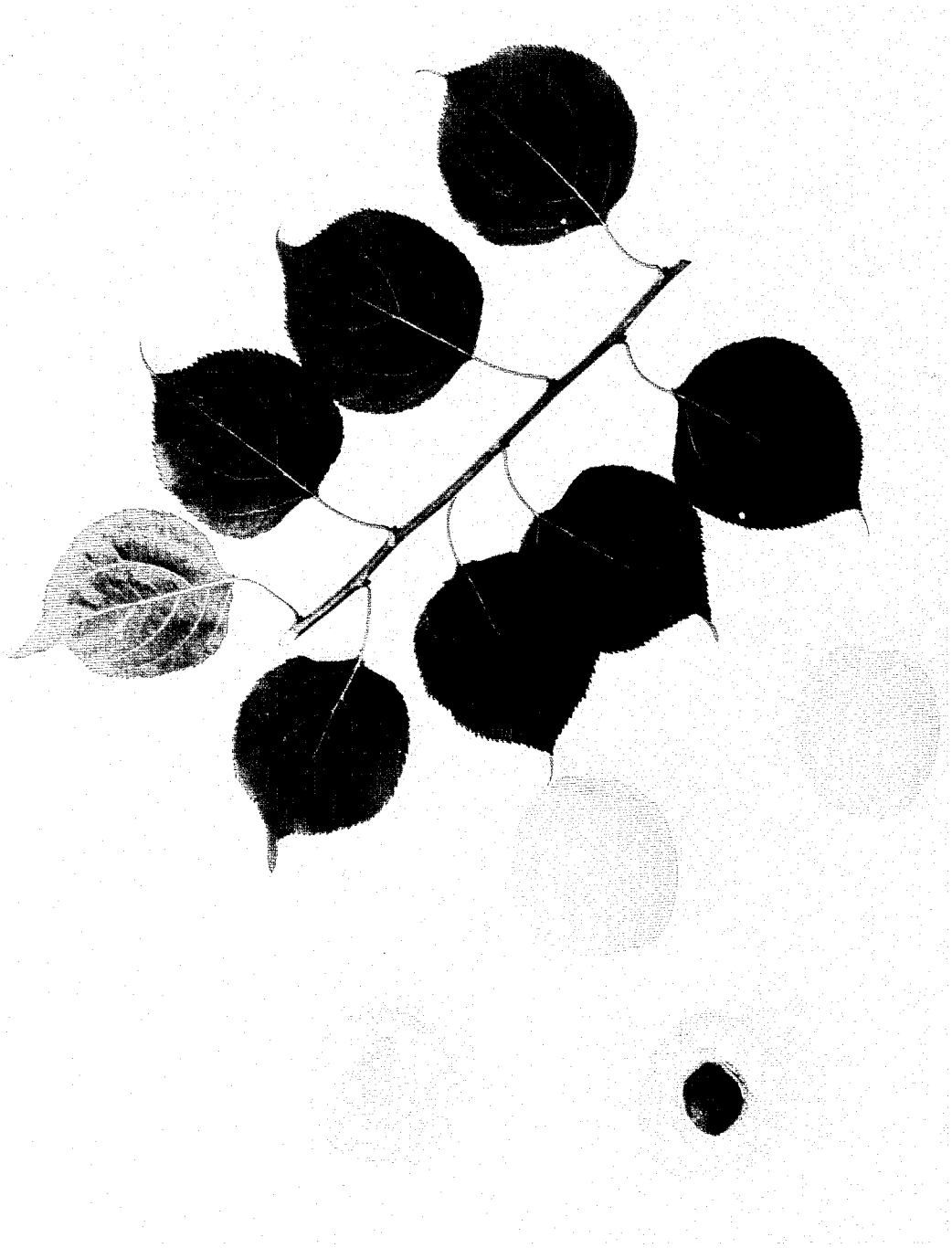
INVENTOR
Frederic W. Anderson
BY
Webster & Webster
ATTORNEYS

United States Patent Office

Plant Pat. 2,877
Patented Apr. 1, 1969

2,877
APRICOT TREE

Frederic W. Anderson, Merced, Calif., assignor to The Burchell Nursery, Inc., Modesto, Calif., a corporation of California

Filed Sept. 14, 1967, Ser. No. 667,870
Int. Cl. A01h *5/08*
U.S. Cl. Plt.—39 1 Claim

ABSTRACT OF THE DISCLOSURE

A cultivar of apricot tree which is a sibling of and, in general, closely resembles the Modesto (United States Plant Patent No. 2,543).

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of apricot tree resulted from my endeavors in the conduct of such plant breeding program.

*Origin of the variety*

The herein claimed variety of apricot tree was originated by me, at my experimental nursery and orchard located as aforesaid, as a second generation seedling of Perfection (unpatented). More particularly, seeds of the self-sterile Perfection were obtained from trees closely adjoining trees of the two leading apricot varieties; viz. the Royal-Blenheim and Tilton (both unpatented). A large number of first generation seedlings, resulting from the planting of such seeds, were grown to maturity. From such of these first generation seedlings that evidenced desirable characteristics, seeds were obtained and planted, and from the resulting second generation seedlings the present variety was selected as being distinctive and having commercially desirable features as hereinafter described.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

While generally similar to the Modesto in tree and fruit, the present variety of apricot tree is new and distinct in the following respects:

In comparison to the Modesto, the present variety is about two to three days later, both as to the time of full bloom of the flowers and the ripening period of the fruit. Also, full bloom occurs about three days before the Royal-Blenheim.

Further, the flesh has greater firmness than that of both the Modesto and Royal-Blenheim; this being of substantial commercial advantage for the reason—established by extended tests—that there is a lesser tendency for the fruit, when canned, to soften or "break down" in the can. Thus, the fruit, after canning, holds its shape and texture for a longer period of time.

*Brief description of the drawing*

The drawing is an illustration, by photographic reproduction in color, of fruit of the variety, together with a twig with leaves; the view including one fruit cut in half in the suture plane, with the stone remaining in one half.

*Description of the variety*

The botanical details of this new and distinct variety of apricot tree—with color definitions (except those in common color terms) referenced to Maerz and Paul Dictionary of Color—are as follows:

Tree:
- *Size.*—Medium.
- *Vigor.*—Vigorous.
- *Growth.*—Spreading.
- *Production.*—Productive.
- *Bearing.*—Regular bearer.

Trunk: Size—medium.

Branches:
- *Size.*—Medium.
- *Color.*—Red to green.
- *Lenticels.*—Number—medium.

Leaves:
- *Size.*—Large. Average length—3¼". Average width—2⅝".
- *Form.*—Cordate; acutely pointed.
- *Thickness.*—Medium.
- *Texture.*—Smooth.
- *Margin.*—Crenate; finely serrate.
- *Petiole.*—Medium length—average ⅞". Medium thickness.
- *Glands.*—Number and position—usually 2 on blade, and 2 to 6 on petiole. Alternate; small; globose; green.
- *Color.*—Top side—Medium Green (23–L–7). Under side—Lighter Green (22–L–7).

Flower buds:
- *Size.*—Medium.
- *Length.*—Short.
- *Form.*—Conic.

Flowers:
- *Blooming period.*—Usually about 2 to 3 days after Modesto, and about 3 days before Royal-Blenheim.
- *Size.*—Medium.
- *Color.*—Light pink before buds open; almost completely white at full bloom; sepals reddish.

Fruit:
- *Maturity when described.*—Eating ripe—June 28, 1967.
- *Date of first picking.*—June 25, 1967.
- *Date of last picking.*—July 3, 1967.
- *Size.*—Uniform; large to medium. Average diameter axially—2". Average transversely in suture plane—2". Average lateral thickness—1½".
- *Form.*—Uniform; symmetrical; globose to oblong; compressed laterally.
- *Suture.*—Distinct; extends from base to apex.
- *Cavity.*—Rounded. Average depth—⅜". Average breadth—⅝".
- *Base.*—Rounded.
- *Apex.*—Short; depressed.
- *Pistil point.*—Absent.

Skin:
- *Thickness.*—Medium.
- *Texture.*—Medium.
- *Tenacity.*—Tenacious to flesh.
- *Tendency to crack.*—None noted.
- *Down.*—Scant; short.
- *Color.*—Normal Apricot (10–L–8) shading slightly to Red (5–L–8) on sunny side.

Flesh:
- *Amygdalin.*—Moderate.
- *Texture.*—Firm; crisp; meaty.
- *Fibers.*—Few.
- *Ripens.*—Evenly.
- *Flavor.*—Subacid; delicate.

Flesh:—Continued

*Eating quality.*—Good to best.

*Color.*—Normal Apricot (9–L–8).

Stone:

*Type.*—Free.

*Fibers.*—Short.

*Size.*—Medium. Average length—1″. Average breadth—¾″. Average thickness—½″.

*Form.*—Oval.

*Base.*—Straight.

*Apex.*—Rounded.

*Sides.*—Equal.

*Ridges.*—Continuous.

*Dorsal edge.*—Full, with deep broad groove.

*Tendency to split.*—Very slight.

*Color.*—Brown (8–E–12).

Use: Market; dessert; canning.

Keeping quality: Good.

Shipping quality: Good.

The apricot tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of apricot tree, substantially as illustrated and described, which bears general resemblance in tree and fruit to the Modesto but is characterized, in comparison, by a blooming period about two to three days later, by a ripening period about two to three days later, and by fruit having greater firmness of flesh than either said Modesto or the Royal-Blenheim whereby the fruit better holds its shape and texture after canning.

No references cited.

ROBERT E. BAGWILL, *Primary Examiner.*